Figure 1:
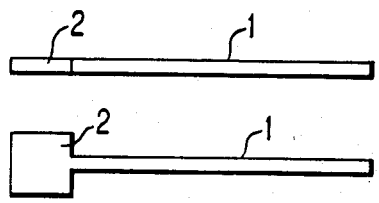

United States Patent [19]

Morton

[11] Patent Number: 4,639,136

[45] Date of Patent: Jan. 27, 1987

[54] ELECTROTHERMAL ATOMISER

[75] Inventor: Stephen F. N. Morton, Cambridge, England

[73] Assignee: U.S. Philips Corporation, New York, N.Y.

[21] Appl. No.: 738,003

[22] Filed: May 28, 1985

[30] Foreign Application Priority Data

Jun. 20, 1984 [GB] United Kingdom ............... 8415682

[51] Int. Cl.$^4$ .............................................. G01N 21/74
[52] U.S. Cl. ..................................... 356/312; 356/244
[58] Field of Search ............................. 356/312, 244

[56] References Cited

U.S. PATENT DOCUMENTS

| 4,406,540 | 9/1983 | Grossman et al. | 356/312 |
| 4,443,105 | 4/1984 | Huber et al. | 356/312 |
| 4,534,646 | 8/1985 | Tamm et al. | 356/312 |
| 4,537,506 | 8/1985 | Lersmacher et al. | 356/312 |
| 4,547,069 | 10/1985 | Lermacher et al. | 356/244 |
| 4,548,497 | 10/1985 | Huber et al. | 356/312 |

FOREIGN PATENT DOCUMENTS 2023336 12/1971 Fed. Rep. of Germany ...... 356/312

OTHER PUBLICATIONS

Giri et al., *Analyst*, vol. 108, Feb. 1983, pp. 244–253.

*Primary Examiner*—F. L. Evans
*Attorney, Agent, or Firm*—Paul R. Miller

[57] ABSTRACT

An electrothermal atomiser comprises a graphite cuvette (5) in which a probe (6) is inserted by an actuator (7). The cuvette is gripped by jaws (15) through which an electrical power supply is connected to resistively heat the cuvette (5). The probe (6) is formed from electrographite and may have a flat or profiled head portion on which the sample is deposited by means of a dosing tube (8).

6 Claims, 6 Drawing Figures

ELECTROTHERMAL ATOMISER

The invention relates to an electrothermal atomiser for a spectrophotometer with the atomiser comprising a hollow body of electrically conductive material, means for depositing a sample on a probe, means for inserting the probe into the interior of the hollow body, and means for passing an electrical current through the hollow body to heat the interior of the hollow body to a temperature which is sufficient to atomise the sample.

Such an atomiser is disclosed in UK Patent Application No. 2136144A. In this atomiser the probe was formed of pyrolytic graphite as was the preferred form of hollow body (or cuvette). An atomiser as set forth in the opening paragraph has also been disclosed in UK Patent Application No. 2088582A in which the probe (or sample carrier) is formed of graphite of unspecified type. UK Patent Application No. 2071845 discloses such an atomiser in which the probe is in the form of a wire (tungsten) filament. UK Patent Application No. 2113128A discloses a probe made from glassy carbon.

It has been found that probes made from pyrolytic graphite and glassy carbon and probes coated with pyrolytic graphite suffer from the disadvantage of sample spreading when samples contain more than about 0.5% v/v of nitric acid. The reduced surface tension of such solutions causes the sample to spread irreproducibly up the probe stem during the drying phase. Various proposals have been made in an attempt to overcome this problem. The initial experiments were conducted with the probe inserted into the cuvette through a slot in the wall in a manner as described in UK Patent Application No. 2136144A. With this configuration only the probe head is heated significantly during the drying phase, while the stem, outside the cuvette, remains cool. It was thought that the sharp temperature gradient along the probe could be responsible for the spreading phenomenon, as the liquid sample would tend to travel to the cooler region outside the cuvette.

The alternative configuration, the 'end entry' probe, allows the probe to enter the cuvette parallel to its long axis. It is therefore no longer necessary to cut a slot in the cuvette, and so improved cuvette lifetimes and sensitivity would be expected. The temperature gradient along the probe would now also be much less steep, as a large part of the stem as well as the head would be heated. It was throught that the spreading problem would therefore be alleviated, and that even if some spreading did occur, as much more of the probe stem would be introduced into the hot zone during the atomisation phase, the effects might be less significant.

Such an arrangement was tried and initial results using glassy carbon probes with a pyrolytic graphite coating were promising. However on repeating the measurement it was found that the performance deteriorated until there was no significant improvement in controlling sample spreading over the front entry system.

Other approaches tried were to use microporous glassy carbon probes with either the head or the stem pyrolytically coated. It was found that coating the head and leaving the stem uncoated gave no significant advantage over a fully coated probe while coating the stem and leaving the head uncoated gave a worse performance.

A further approach attempted was to deposit the sample onto a hot probe. However, with the arrangement used in which the probe is heated by the cuvette it was not found to be practicable as the sample boiled inside the pipette before it could be deposited on the probe. It is considered, however, that this arrangement could be advantageous if the probe is heated independently of the cuvette.

All these attempts at solving the problem of sample spreading have proved unsuccessful and appear to make the use of probe atomisation unsatisfactory for all but a minority of practical samples.

It is an object of the invention to enable the provision of an electrothermal atomiser in which the sample is atomised off a probe inserted into a hollow body which is capable of handling samples with a low surface tension such as acid samples.

The invention provides an electrothermal atomiser as set forth in the opening paragraph characterised in that at least the portion of the probe on which the sample is to be deposited is formed from electrographite.

It has been found that the use of electrographite for the probe substantially reduces the problem of sample spreading. The use of RWO grade spectrographic electrographite manufactured and sold by Ringsdorff G.m.b.H of Bonn-Badgodesberg, West Germany has been found to be effective.

The portion of the probe on which the sample is to be deposited may comprise a recess for containing the sample. This reduces the spreading problems involved with samples such as organic solvents or body fluids containing surfactants.

The probe may comprise a head portion with for receiving the sample and a stem portion, a step being formed between the head and stem portions. This helps to reduce spreading of the sample up the probe stem but suffers from the disadvantage that a double measurement peak is obtained. This is caused by part of the sample running back against the step and drying in the corner while part remains on the probe head. The temperature of the step region lags behind that of the head as it has a greater mass so that the samples in the two areas will be atomised at different times producing the double peaks.

Figure 2:
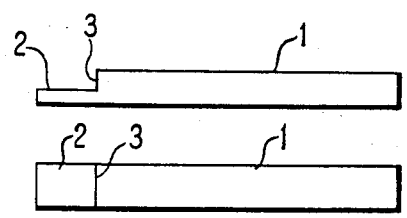
Figure 3:
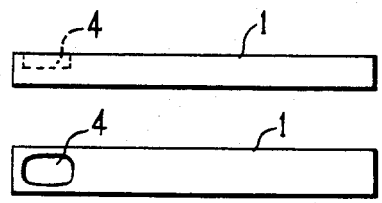
Figure 4:
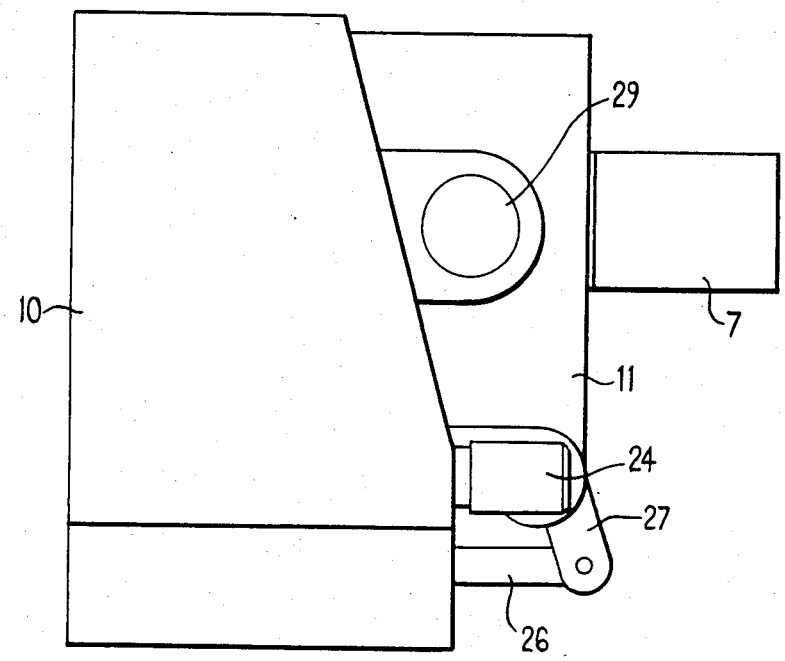
Figure 5:
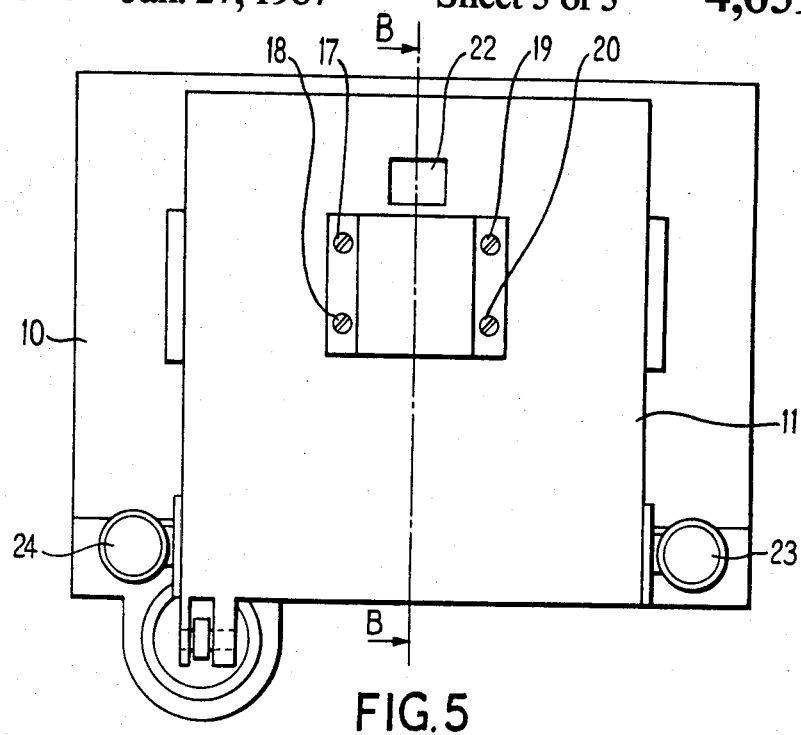
Figure 6:
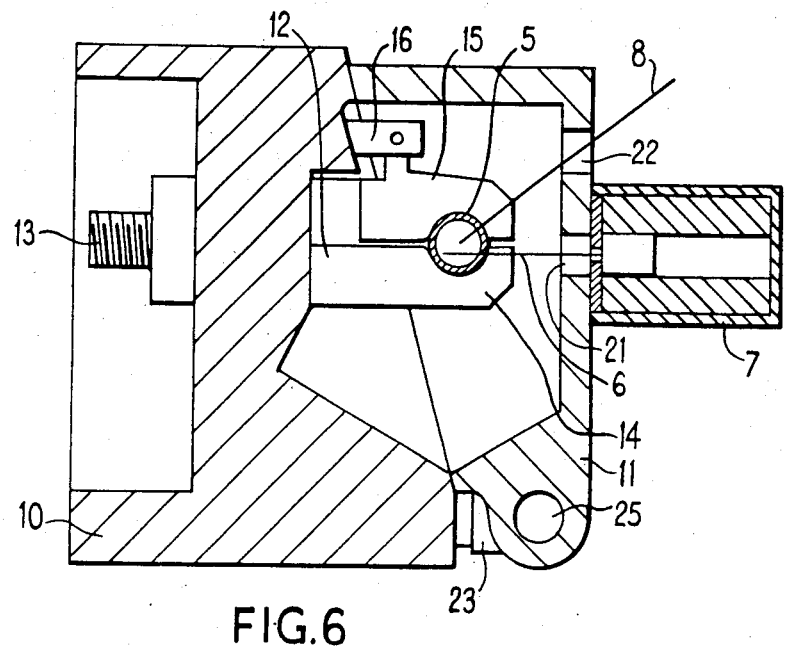

Embodiments of the invention will now be described, by way of example, with reference to the accompanying drawings, in which:

FIG. 1 shows plan and elevation views of a first construction of a probe for use in an electrothermal atomiser according to the invention, FIG. 2 shows plan and elevation views of a second construction of a probe for use in an electrothermal atomiser according to the invention, FIG. 3 shows plan and elevation views of a third construction of a probe for use in an electrothermal atomiser according to the invention, FIG. 4 is a side elevation of an electrothermal atomiser according to the invention for an atomic absorption spectrophotometer, FIG. 5 is a front elevation of the atomiser shown in FIG. 4, and FIG. 6 is a cross-sectional view on line B—B of FIG. 5.

As shown in FIG. 1 the probe comprises a stem portion 1 and a flat head portion 2. At least the head portion 2 is formed from electrographite, a suitable grade of which is that sold by Ringsdorff G.m.b.H of Bonn-Badgodesberg, West Germany under the reference RWO. Conveniently the whole probe may be formed from a single piece of electrographite. Alternatively the stem may be formed from a material having a lower thermal conductivity which has the advantage of increasing the speed of heating of the head portion as a smaller amount of heat is conducted along the stem.

FIG. 2 shows an alternative form of probe which comprises a stem portion 1 and a head portion 2. The stem portion 1 is relatively thick so that it forms a step 3 between the stem and head portion. This form of probe, however, suffers from the disadvantage discussed hereinbefore that a double measurement peak is produced.

FIG. 3 shows a further alternative form of probe which comprises a stem portion 1 and a head portion 2 which is provided with a recess or dimple 4. The recess 4 is provided for samples such as organic solvents or body fluids containing surfactants.

FIGS. 4, 5 and 6 show a cuvette 5, a probe 6, and an actuator 7 mounted in and on an atomiser for an atomic absorption spectrophotometer. The probe 6 takes the form of a probe as described with reference to FIGS. 1, 2 or 3 and the cuvette is a hollow cylindrical graphite body. The atomiser comprises a body 10 having a hinged door 11. Within the atomiser body 10 two contact jaws, one of which is shown at 12 grip each end of the cuvette 5. The jaws have electrical connection terminals, one of which is shown at 13, to which an electrical current source may be connected for passing a current through the cuvette. The contact jaw 12 comprises a fixed lower portion 14 and a pivotted upper portion 15 which can be pivotted by moving a member 16 into the body 10, horizontally to the left in the embodiment shown in FIG. 6. The actuator 7, which in this embodiment is in the form of a solenoid but which may be, for example a motor and cam drive, is attached to the door 11 of the furnace by four screws 17 to 20 and the probe 6 passes through an aperture 21 in the door 11. A further aperture 22 is provided in the front of the door 11 through which a dosing tube 8 may be inserted to deposite a sample on the probe. Preferably the aperture 22 is closed when the cuvette is being heated so that the escape of protective gas is reduced. Since the cuvette 5 is normally made of carbon it is necessary to prevent rapid oxidation when it is heated to the atomising temperatures which may be in the region of 3000° C. Consequently it is customary to provide a flow of inert gas over and through the cuvette 5.

The door 11 is hinged along its bottom edge, and is mounted between two fixed members 23 and 24 by a shaft 25 having ends free to rotate in the fixed members 23 and 24. The opening and closing of the door 11 is performed by a rod 26 pivotally connected to a lug 27 on the door 11 and operated by a piston in a cylinder. A quartz window 29 is set in both sides of the door 11 with the quartz windows being aligned with the longitudinal axis of the tubular body 6. The door 11 is normally kept closed and only opened to replace the cuvette when it has reached the end of its life.

While the arrangement described shows an atomiser as disclosed in UK Patent Application No. 2136144A the invention is not limited to such an arrangement. A probe made of electrographite can advantageously be applied to any atomiser in which the sample is atomised off a probe. The particular shape of the head portion of the probe may also be adapted to suit the form of atomiser used, in particular for either front or end entry i.e. transverse or parallel to the longitudinal axis of the cuvette.

I claim:

1. An electrothermal atomizer for a spectrophotometer, said atomizer comprising a hollow body of electrically conductive material, probe means for holding a sample in the interior of said hollow body, dosing means for depositing said sample onto said probe means within said interior, actuator means for inserting said probe means into said interior, and means for passing an electrical current through said hollow body to heat said interior to a temperature sufficient to atomize said sample, wherein at least a portion of said probe means on which said sample is deposited is of electrographite.

2. An electrothermal atomizer according to claim 1, wherein said probe means is entirely formed from electrographite.

3. An electrothermal atomizer according to claim 1 or 2, wherein said portion includes a recess for containing said sample.

4. An electrothermal atomizer according to claim 3, wherein said probe means includes a head portion for receiving said sample, and a steam portion for insertion into said hollow body.

5. An electrothermal atomizer according to claim 1 or 2, wherein said probe means includes a head portion for receiving said sample, and a stem portion for insertion into said hollow body, said probe means further including a step between said head portion and said stem portion.

6. An electrothermal atomizer according to claim 1 or 2, wherein said hollow body is tubular and open at both ends, and wherein said hollow body has a wall containing a slot, said probe means being inserted through said slot into said hollow body in a direction perpendicular to the longitudinal axis of said hollow body.

* * * * *

UNITED STATES PATENT AND TRADEMARK OFFICE
CERTIFICATE OF CORRECTION

PATENT NO. : 4,639,136
DATED : Jan. 27, 1987
INVENTOR(S) : Stephen F.N. Morton

It is certified that error appears in the above-identified patent and that said Letters Patent is hereby corrected as shown below:

Column 3, line 38, change "deposite" to --deposit--

Column 4, line 36, change "steam" to --stem--

Signed and Sealed this

Seventeenth Day of November, 1987

Attest:

DONALD J. QUIGG

*Attesting Officer*    *Commissioner of Patents and Trademarks*